(12) United States Patent
Oba et al.

(10) Patent No.: US 6,786,100 B2
(45) Date of Patent: Sep. 7, 2004

(54) DEVICE FOR MEASURING PHYSICAL PROPERTIES OF ELASTIC BODIES

(75) Inventors: Ai Oba, Yokohama (JP); Yasutomo Nishimori, Yokohama (JP)

(73) Assignee: Pola Chemical Industries Inc., Shizuoka (JP)

( * ) Notice: Subject to any disclaimer, the term of this patent is extended or adjusted under 35 U.S.C. 154(b) by 0 days.

(21) Appl. No.: 10/182,020

(22) PCT Filed: Jan. 18, 2001

(86) PCT No.: PCT/JP01/00304
§ 371 (c)(1),
(2), (4) Date: Jul. 19, 2002

(87) PCT Pub. No.: WO01/52724
PCT Pub. Date: Jul. 26, 2001

(65) Prior Publication Data
US 2003/0005781 A1 Jan. 9, 2003

(30) Foreign Application Priority Data
Jan. 19, 2000  (JP) .................................... 2000-009671

(51) Int. Cl.⁷ ............................................... G01N 3/08
(52) U.S. Cl. ...................................................... 73/818
(58) Field of Search .......................... 73/818, 788, 790, 73/795, 819, 823, 825

(56) References Cited

U.S. PATENT DOCUMENTS 5,123,284 A * 6/1992 Edinburgh et al. ............. 73/826
5,564,573 A * 10/1996 Palm et al. .................. 209/518
5,571,973 A * 11/1996 Taylot ..................... 73/862.046
6,427,524 B1 * 8/2002 Raspante et al. ............. 73/45.4

FOREIGN PATENT DOCUMENTS

| JP | 61-181438 | 8/1986 |
| JP | 01-115342 | 5/1989 |

* cited by examiner

Primary Examiner—Max Noon
(74) Attorney, Agent, or Firm—Knobbe, Martens, Olson & Bear, LLP

(57) ABSTRACT

A device for measuring mechanical properties of an elastic body, comprising:
  at least two contacts adapted to contact a surface of an elastic body to be measured, at least one of said contacts being a movable contact;
  a drive section for moving said movable contact;
  a control section for controlling an action of said drive section;
  a detecting section for detecting a stress generated by the movement of said contact as an electric signal; and
  a processing section for processing the electric signal for the stress detected by said detecting section and an amount of movement of said movable contact,
wherein the action of said contacts making contact with the surface of said elastic body includes a closing action of the two of the contacts and a stationarily holding action after the closing action.

8 Claims, 11 Drawing Sheets

DEVICE FOR MEASURING PHYSICAL PROPERTIES OF ELASTIC BODIES

This is the U.S. National Phase under 35 U.S.C. §371 of International Application PCT/JP01/00304, filed Jan. 18, 2001, which claims priority of Japanese Patent Application No. 2000-9671, filed Jan. 19, 2000.

TECHNICAL FIELD

The present invention relates to a device for appropriately measuring mechanical properties of elastic bodies such as mechanical properties of a skin.

BACKGROUND ART

Conventionally, as a device for measuring mechanical properties of elastic bodies such as a skin, there are known devices, such as a so-called Cutometer for bringing an adherent probe into close contact with the skin and sucking and exhausting a gas therefrom to measure a degree of deformation of the surface of the skin caused thereby, and a Twistometer for rotating a contact on a surface of the skin to measure a stress generated from the skin side in response to the rotation. In such devices, there are difficulties in that measurement cannot be performed taking into account directivity of the skin and quantitative measurement cannot be performed in the strict sense of the word. In addition, a force applied to the skin by these devices is not a force applied to the skin in a daily life.

As a device capable of measuring extending ability of the skin in an arbitrary direction, there is known an extensometer (Acta. Derm. Venereol. (Stockh), 1997, 77:416–419). However, the only mechanical property value that is measured by this device is extending ability.

DISCLOSURE OF THE INVENTION

The inventors have found that a collagen fiber structure exists in dermis of the skin and, therefore, there is a significant difference of mechanical properties according to directions. Therefore, meaningful mechanical property values cannot be measured in the skin unless directivity of measurement is controlled strictly. Moreover, the extensometer for pulling the skin to measure its extending ability is not regarded as an optimum machine for measuring mechanical properties in examining relationship between mechanical properties and wrinkle formation.

The present invention has been devised under such circumstances, and it is an object of the present invention to provide a device for measuring mechanical properties of elastic bodies that is capable of strictly controlling a direction of measurement and measuring mechanical properties or the like that are more related to wrinkle formation on a surface of an elastic body such as a skin.

In view of such actual circumstances, the inventors concentrated their efforts on researches and, as a result, found that such measurement is possible by using a device for measuring mechanical properties of elastic bodies that is capable of analyzing deformation of the skin due to an external force imitating a force that a facial skin of a human is actually subjected to in a daily life, that is, measuring and analyzing a stress of the skin when the skin is contracted. That is, the present invention relates to the following technology.

(1) A device for measuring mechanical properties of elastic bodies, comprising: at least two contacts adapted to contact a surface of an elastic body to be measured, at least one of the contacts being movable; a drive section for moving the movable contact; a control section for controlling an action of the drive section; a detecting section for detecting a stress generated by the movement of the contact as an electric signal; and a processing section for processing the electric signal for the stress detected by the detecting section and an amount of movement of the movable contact, in which the action of the contacts making contact with the surface of the elastic body includes a closing action of the two of the contacts and a stationarily holding action after the closing action.

(2) A device for measuring mechanical properties of elastic bodies according to (1), which further comprises a display section for displaying data processed by the processing section.

(3) A device for measuring mechanical properties of elastic bodies according to (1) or (2), wherein the elastic body to be measured is a skin.

(4) A device for measuring mechanical properties of elastic bodies according to any one of (1) to (3), wherein a probe is comprised of the contacts, the drive section and the detecting section, and the device comprises an arm section for holding a position of the probe.

(5) A device for measuring mechanical properties of elastic bodies according to any one of (1) to (4), which comprises a holding section for holding the elastic body to be measured.

(6) A device for measuring mechanical properties of elastic bodies according to any one of (1) to (5), wherein the contacts are fixed on the surface of the elastic body.

BEST MODE FOR CARRYING OUT THE INVENTION

Figure 1:
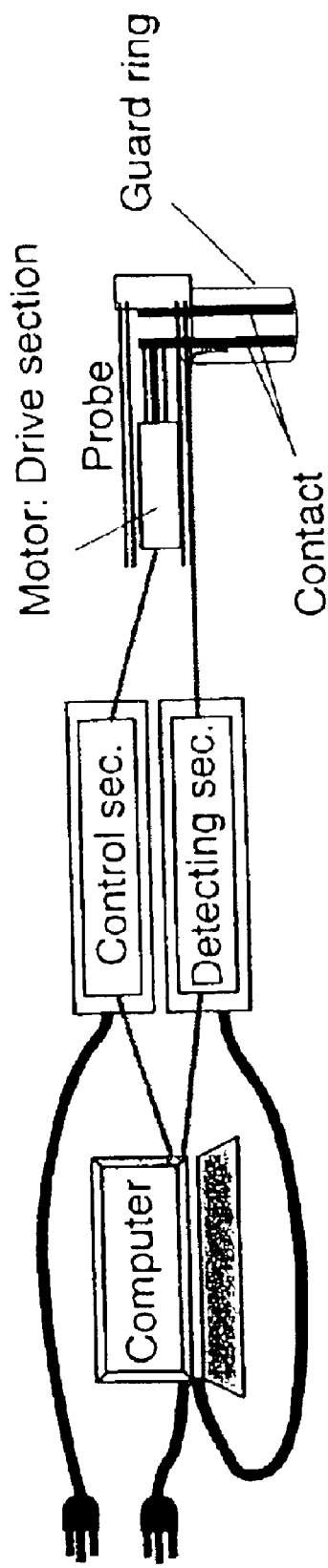
FIG. 1 is a schematic view showing a device of Embodiment 1.

The present invention will be hereinafter described in detail centering on embodiments.

(1) Contacts of the Device for Measuring Mechanical Properties of Elastic Bodies of the Present Invention The device for measuring mechanical properties of elastic bodies of the present invention is characterized by having at least two contacts, at least one of which is movable. This is because a distance between the contacts is changed, whereby an elastic body on which the contacts are placed is deformed and a change in a stress caused in accordance with the deformation shows characteristics of mechanical properties of the elastic body. In this case, when two contacts are provided, one of the contacts may be stationary and the other may be movable or both of the contacts may be movable. In the case in which both the contacts are movable, analysis of a change in a stress becomes more complicated than the former case. In addition, a device having three or more contacts to measure and analyze a change in a stress with respect to a more complicated deformation pattern also belongs to the technical scope of the device for measuring mechanical properties of elastic bodies of the present invention. Further, both the movable and unmovable contacts are preferably fixed on the elastic body by adhesive or a viscous material during measurement. However, the contacts can be used with their contacting parts made in a shape having a large coefficient of friction instead of being fixed if evaluation of sliding resistance on the elastic body is taken into account.

(2) A Drive Section of the Device for Measuring Mechanical Properties of Elastic Bodies of the Present Invention The device for measuring mechanical properties of elastic bodies of the present invention has a drive section. The drive section functions as a power source for moving the above-described movable contact. As such a power source, a motor or the like can be preferably mentioned. For example, rotational motion generated by a motor is converted to linear motion by a cam, a pulley and the like to cause the movable contact to move linearly. An amount of movement of the movable contact driven by the drive section is monitored according to motion characteristics of a movable portion such as position coordinates and the number of rotations of the contact.

(3) A Control Section of the Device for Measuring Mechanical Properties of the Present Invention Kinetic energy generated by the drive section causes the contact to move, for example, linearly. Such movement is controlled by a control section. This is because the surface of the elastic body may be destroyed if an excessive amount of movement is applied to the contact or reliability of a measurement value may be damaged if motion control is not performed properly. Such control is preferably performed based on results of the above-described monitoring of an amount of movement. In addition, such control is managed by a computer or the like and becomes means for specifying a motion pattern (action) of the movable contact. As such a computer, a commercially available personal computer can be used.

The motion pattern of the movable contact in the device for measuring mechanical properties of the present invention is set such that the action of the contact making contact with the surface of the elastic body includes a closing action of the two of the contacts and a stationarily holding action after the closing action. Preferably, a motion pattern is used in which a basic cycle consisting of the closing action for reducing a distance between the contacts, the stationarily holding action for maintaining the distance between the contacts and a restoring action for restoring the distance between the contacts is repeated, and the motion pattern is analyzed based on a measurement value obtained in the last cycle. An initial value of the distance between the contacts and its reducing value and reducing speed are properly selected according to a type of an elastic body. In the case of a skin, the initial value, the reducing value and the reducing speed are usually selected from the ranges of 3 to 10 mm, 0.5 to 5 mm and 0.5 to 2 mm/sec, respectively. The number of cycles is usually one to five.

Consequently, mechanical properties that are considered to more strongly affect wrinkle formation of elastic bodies such as a skin can be checked.

(4) A Detecting Section of the Device for Measuring Mechanical Properties of Elastic Bodies of the Present Invention A detecting section of the device for measuring mechanical properties of elastic bodies of the present invention detects a stress derived from an elastic body which is caused by movement of the movable contact. The stress detected in this way is transmitted to a processing section discussed bellow as an electric signal. Thus, the stress generated by the movement of the movable contact indicates mechanical properties of the surface of the elastic body and is detected as a numerical value on which various mechanical properties of a elasticity value are reflected according to a motion pattern of the movable contact.

(5) Probe

The above-described contacts, drive section and detecting section preferably constitute a probe as one unit for convenience of use. Such a probe preferably has a structure in which its position is fixed during measurement. As for position fixing means, the probe is preferably attached to an end of a so-called arm which has a metal framework and a spring portion and whose position can be fixed and aligned. With such a structure, a position and a direction of the contact can be changed freely and mechanical properties of the elastic body can be measured in an arbitrary direction with respect to the surface of the elastic body. Such easiness of deformation of the arm should be lower than the movability of the contact. In addition, it is preferable to provide a guard ring surrounding the contact. Influence by parts outside the measurement area can be minimized by providing the guard ring. Examples of the guard ring include a guard ring of a square cylinder shape and a guard ring of a double cylindrical shape, wherein an inner cylinder can slide inside an outer cylinder and the inner cylinder is energized by a spring to protrude more than the outer cylinder. A part contacting the elastic body may be coated with silicone for slip prevention.

(6) A Processing Section of the Device for Measuring Mechanical Properties of Elastic Bodies of the Present Invention A processing section of the device for measuring mechanical properties of elastic bodies of the present invention is a part for processing an amount of movement of the movable contact and a stress generated by the movement of the movable contact. A usual personal computer may be used as the processing section and a special-purpose program may be prepared for the processing. However, the amount of movement (or position coordinates of the movable contact) can be plotted on the X-axis and the stress can be plotted on the Y-axis utilizing, for example, a spreadsheet software such as Excel manufactured by Microsoft Corporation. When such plotting is performed on a graph, a characteristic pattern can be obtained for each elastic body.

The obtained pattern may be analyzed as a whole or a part of the pattern may be analyzed as parameters. For example, in a pattern obtained in a basic cycle consisting of a closing action for reducing a distance between the contacts (step 1), a stationarily holding action for maintaining the distance between the contacts (step 2) and a restoring action (step 3) for restoring the distance between the contacts, the parameters include a maximum stress at the time of reduction in step 1 (Fmax in FIG. 6 or F1 in FIG. 9), a maximum value of a stress attenuating at the time of maintenance in step 2 (Fv in FIG. 6 or F2 in FIG. 9), a maximum value of a stress decreasing at the time of releasing reduction in step 3 (F3 in FIG. 9) and time until the attenuation of the stress reaches F2/e (e=2.718) at the time of maintenance in step 2 (T in FIG. 9).

Moreover, the device for measuring mechanical property of elastic bodies of the present invention preferably has a display section for displaying data processed by the processing section. The display section is, for example, a display.

According to the device for measuring mechanical properties of elastic bodies of the present invention, mechanical properties in a form of a combination of mechanical properties attributable to a surface itself of an elastic body and mechanical properties attributable to an inner structure of the elastic body can be measured. Examples of properties reflected on such mechanical properties include a loss of elasticity due to aging, a change in accordance with photoaging, properties relating to wrinkle formation and the like.

Figure 5:
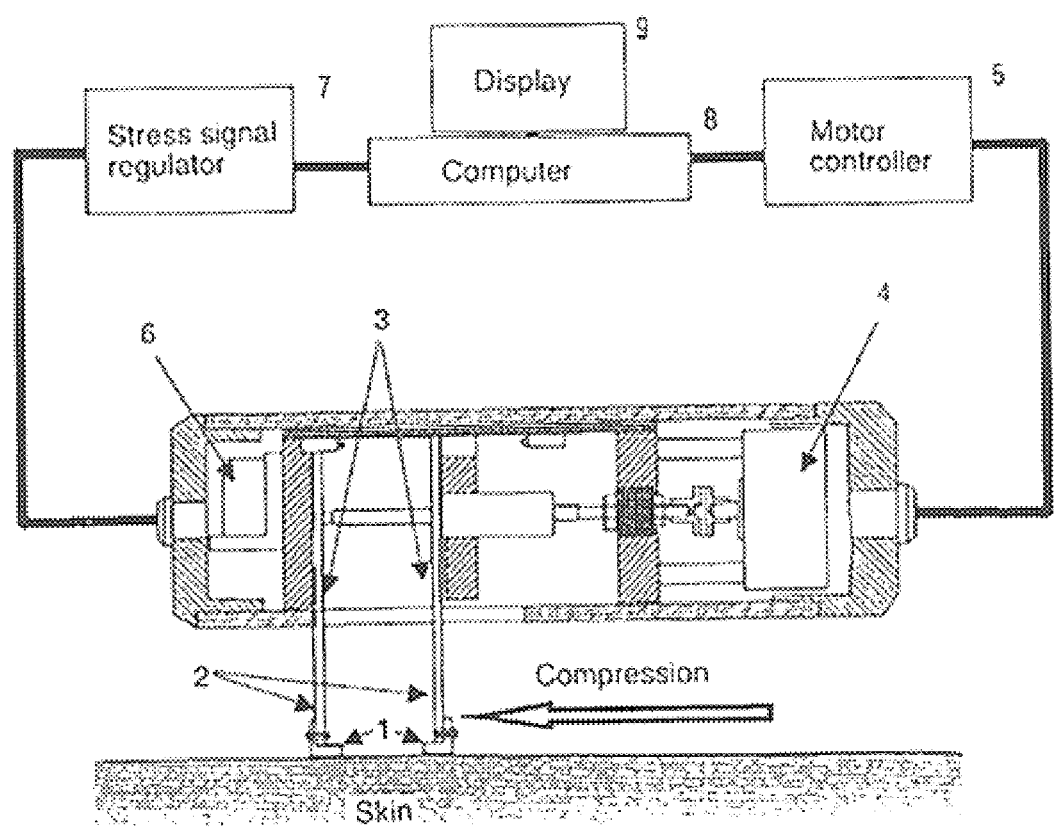
FIG. 5 is a schematic view showing a device of Embodiment 3.

A specific example of the device for measuring mechanical properties of elastic bodies of the present invention will be described with reference to FIG. 5. Contacts are comprised of arms 2 having silicone members 1 for slip prevention at their ends. Strain gauges 3 are attached to probe sides of the arms 2 as detecting sections. One of the arms 2 is made movable by a stepper motor 4 functioning as a drive section. Electric signals from the strain gauges 3 are amplified by a strain amplifier 6 and inputted in a computer 8 functioning as a processing section through a stress signal regulator 7. In addition, the stepper motor 4 is controlled by a motor controller 5 functioning as a control section based on a control signal from the computer 8. An amount of movement of the contact is calculated by the computer 8 from the control signal to the motor controller 5. Then, data processed by the computer 8 are displayed on a display 9. In measuring mechanical properties of the skin, operations are applied to the skin such that the silicone members 1 at the ends of the contacts make contact with the skin and a distance between the arms 2 is reduced and restored by the stepper motor 4 controlled by the motor controller 5, whereby the skin is contracted and restored. An amount of movement of the arms 2 and a force from the skin applied to the arms 2 at this time are inputted in the computer 8 and mechanical properties are measured.

Embodiments

<Embodiment 1>

A device for measuring mechanical properties of elastic bodies shown in FIG. 1 is provided with a probe having one movable contact and one stationary contact and also having a motor (drive section) for driving the movable contact, a control section for controlling forward movement, backward movement and stop of the contact and a detecting section for detecting a stress applied to the contact and, moreover, is provided with a personal computer functioning as a processing section for transmitting a control signal of movement to the control section in accordance with a program, converting this control signal into a position coordinate (X coordinate) and capturing the detected stress as a Y coordinate. As a motion pattern of the movable contact, the two contacts are initially set in positions 4 mm apart from each other and the movable contact approaches the unmovable contact by 1 mm in one second. Thereafter, the movable contact keeps this position for five seconds and returns to the original position 4 mm apart from the unmovable contact in one second. The computer is programmed to repeat this work five times.

<Embodiment 2>

Figure 2:
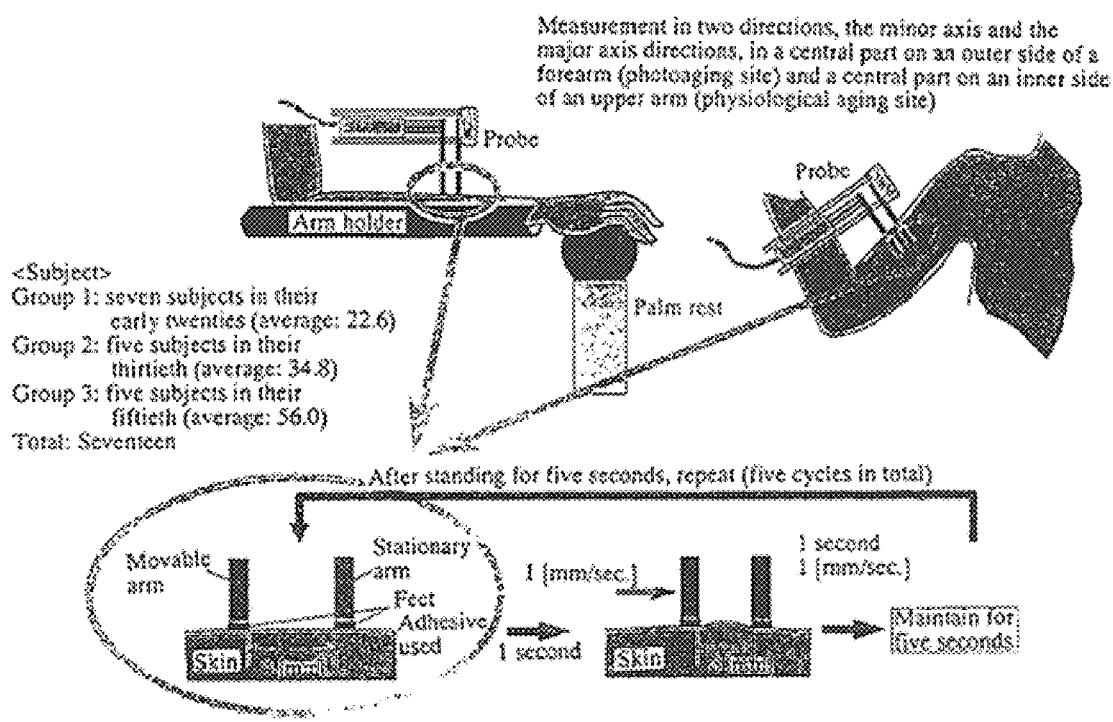
FIG. 2 is a view showing a protocol of Embodiment 2.
Figure 3:
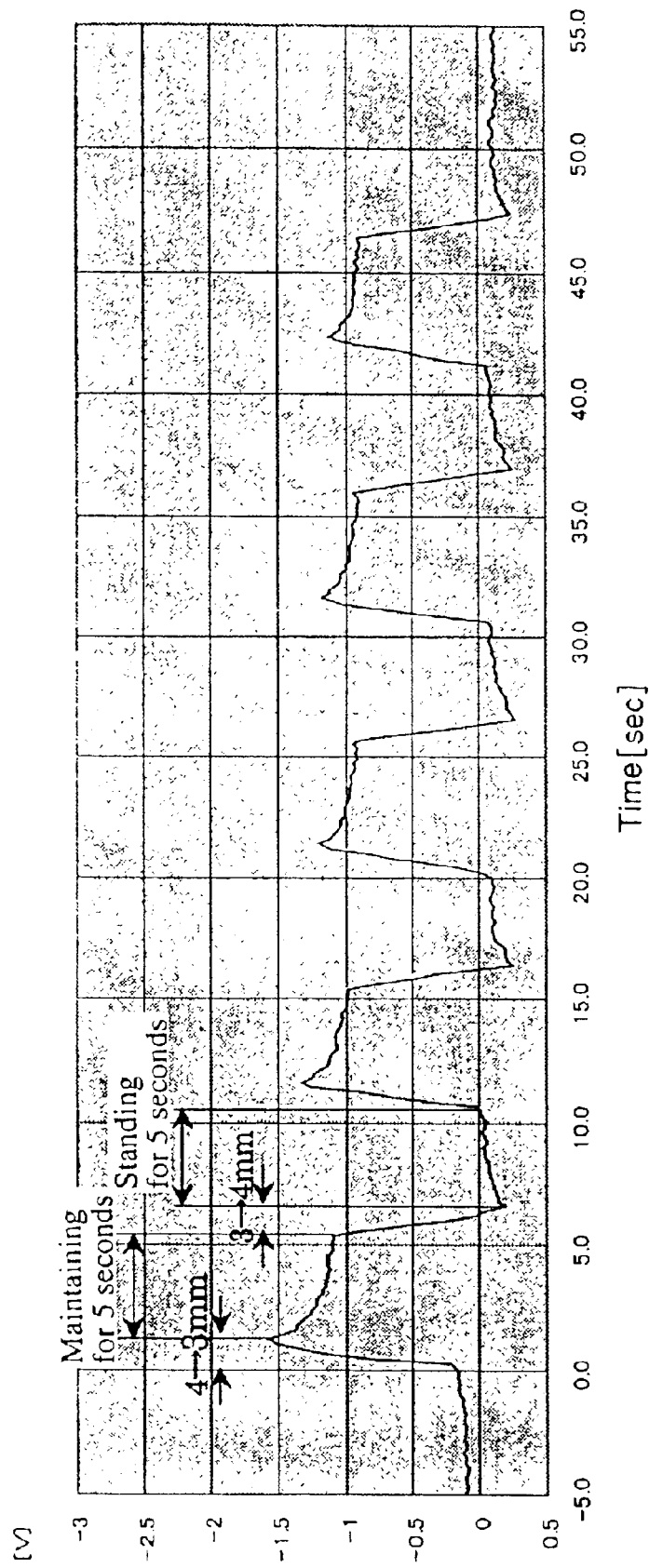
FIG. 3 shows an example of a plot pattern obtained in Embodiment 2, in which measurement is performed in a central part on an outer side of a forearm (at approximately 10 cm from a wrist) and in a short axis direction.
Figure 4:
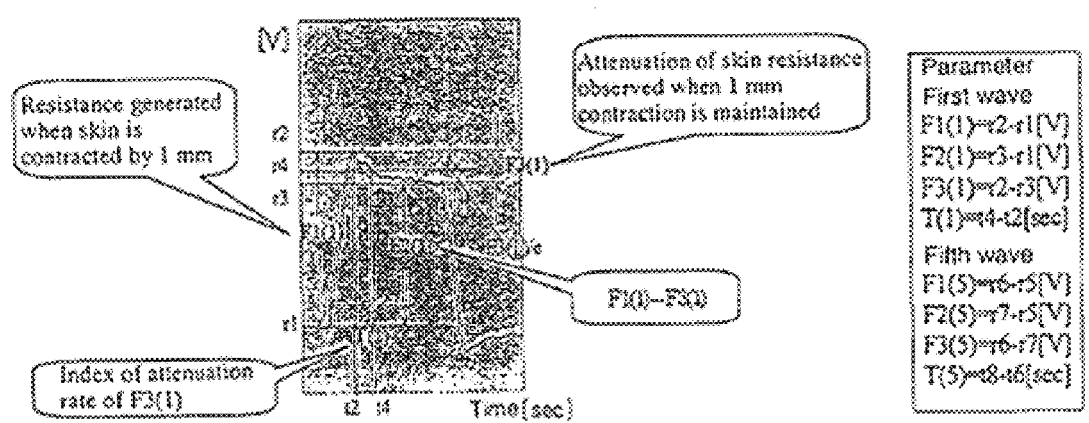
FIG. 4 shows characteristics and parameters of the plot pattern obtained in Embodiment 2, in which r5, r6, r7, r8, t6 and t8 of the fifth wave correspond to r1, r2, r3, r4, t2 and t4 of the first wave, respectively.

Positions of a probe and patterns of a stress were measured in a central part on an outer side of an upper arm (photoaging site) and a central part on an inner side of a forearm (physiological aging site) with respect to seven subjects in their twenties, five subjects in their thirtieth and five subjects in their fiftieth using the device of Embodiment 1 and in accordance with a protocol shown in FIG. 2. An example of a pattern of a graph in such measurement is shown in FIG. 3. Parameters shown in FIG. 4 were calculated from coordinates of each site of this pattern. When relationships among these parameters, measured sites and ages were checked, results shown in Table 1 were obtained. From these results, it can be seen that non-invasive measurement of aging of the skin, which cannot be measured conventionally, can be performed.

TABLE 1

| Parameter | Minor axis measurement | Major axis measurement |
|---|---|---|
| F1(1) | No significant difference | No significant difference |
| F2(1) | No significant difference | ↓* ($p < 0.05$) Physiological aging site |
| F3(1) | No significant difference | No significant difference |
| T(1) | No significant difference | No significant difference |
| F1(5) | No significant difference | ↓* ($p < 0.05$) Physiological aging site |
| F2(5) | No significant difference | ↓** ($p < 0.01$) Physiological aging site |
| F3(5) | No significant difference | ↑* ($p < 0.05$) Photoaging site |
| T(5) | No significant difference | No significant difference |

<Embodiment 3>

A measurement device of this embodiment will be described with reference to FIG. 5. Contacts are constituted by arms 2 having silicone members 1 for slip prevention at their ends. Strain gauges 3 are attached to probe sides of the arms 2 as detecting sections. One of the arms 2 is made movable by a stepper motor 4 functioning as a drive section. Electric signals from the strain gauges 3 are amplified by a strain amplifier 6 and inputted in a computer 8 functioning as a processing section through a stress signal regulator 7. In addition, the stepper motor 4 is controlled by a motor controller 5 functioning as a control section based on a control signal from the computer 8. An amount of movement of the contact is calculated by the computer 8 from the control signal to the motor controller 5. Then, data processed by the computer 8 are displayed on a display 9. A guard ring (which is made of metal and has a square shape with one side being 33 mm and a width of 10 mm) is provided around the contacts in order to minimize influence by portions outside the measurement area.

Motion pattern of the movable contact is the following:

Step 1: The distance between the arms is reduced from 4 mm to 3 mm (1 mm/sec);

Step 2: The distance between the arms is maintained at 3 mm for four seconds; and Step 3: The distance between the arms is returned to 4 mm (1 mm/sec).

Repeat of the cycle: Five times (the pattern is analyzed for the last cycle)

Figure 6:
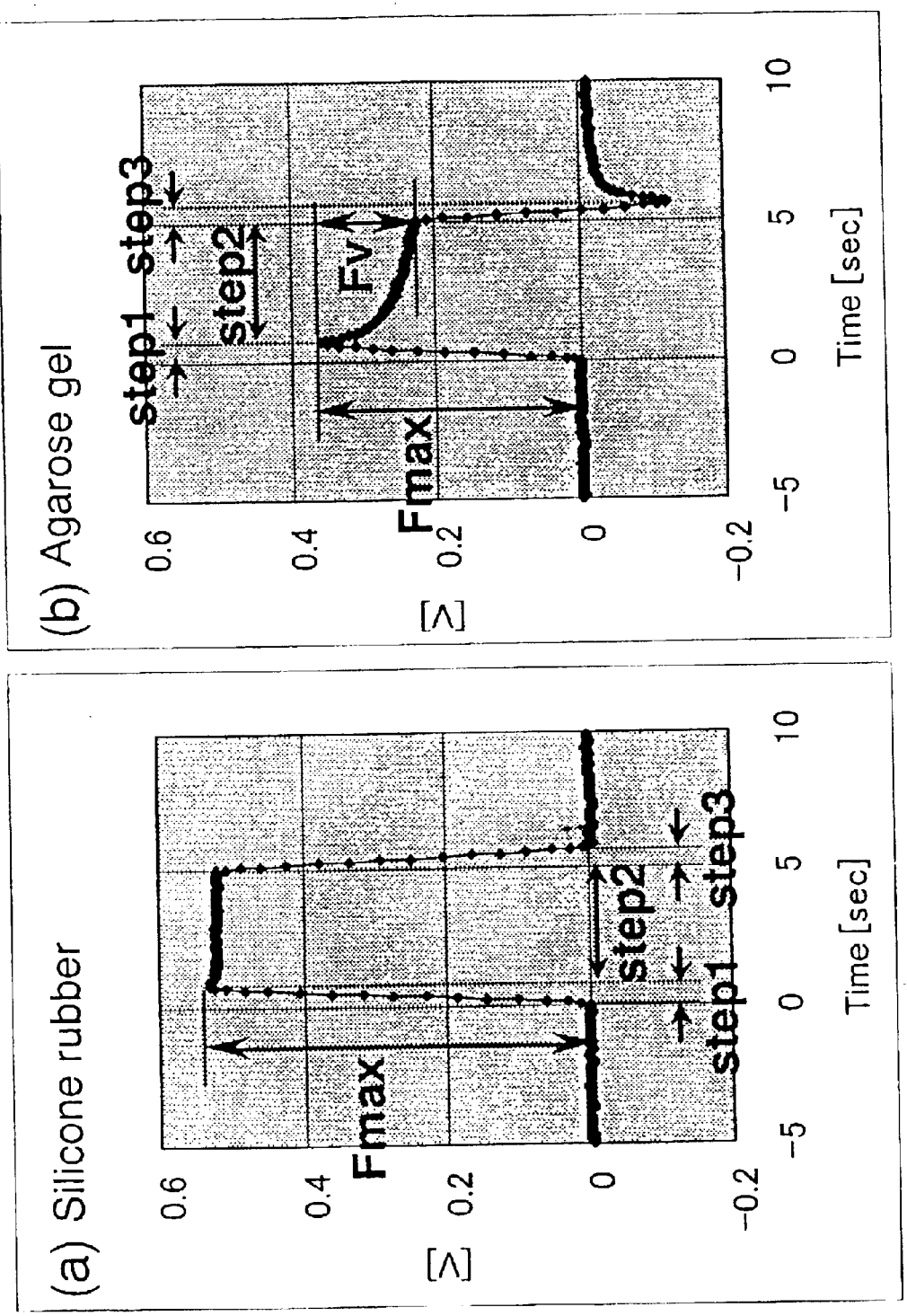
FIG. 6 shows results of measurement of silicone rubber (a) and agarose gel (b) in Embodiment 3.

Silicone rubber was measured as a highly elastic sample and agarose gel was measured as a sample having viscoelasticity using the above-described device. An example of measurement results is shown in FIG. 6. When the pattern was analyzed using a maximum stress at the time of skin contraction (Fmax(V) in FIG. 6), and attenuation of a stress observed in step 2 (Fv(V) in FIG. 6) as parameters, Fv observed in the agarose gel was hardly observed in the silicone rubber. Therefore, Fv is considered to be a parameter relating to viscoelasticity. In addition, it has been found that Fmax increases dependently on hardness of the silicone rubber or concentration of the agarose gel. Therefore, Fmax is considered to be a parameter relating to hardness.

Figure 7:
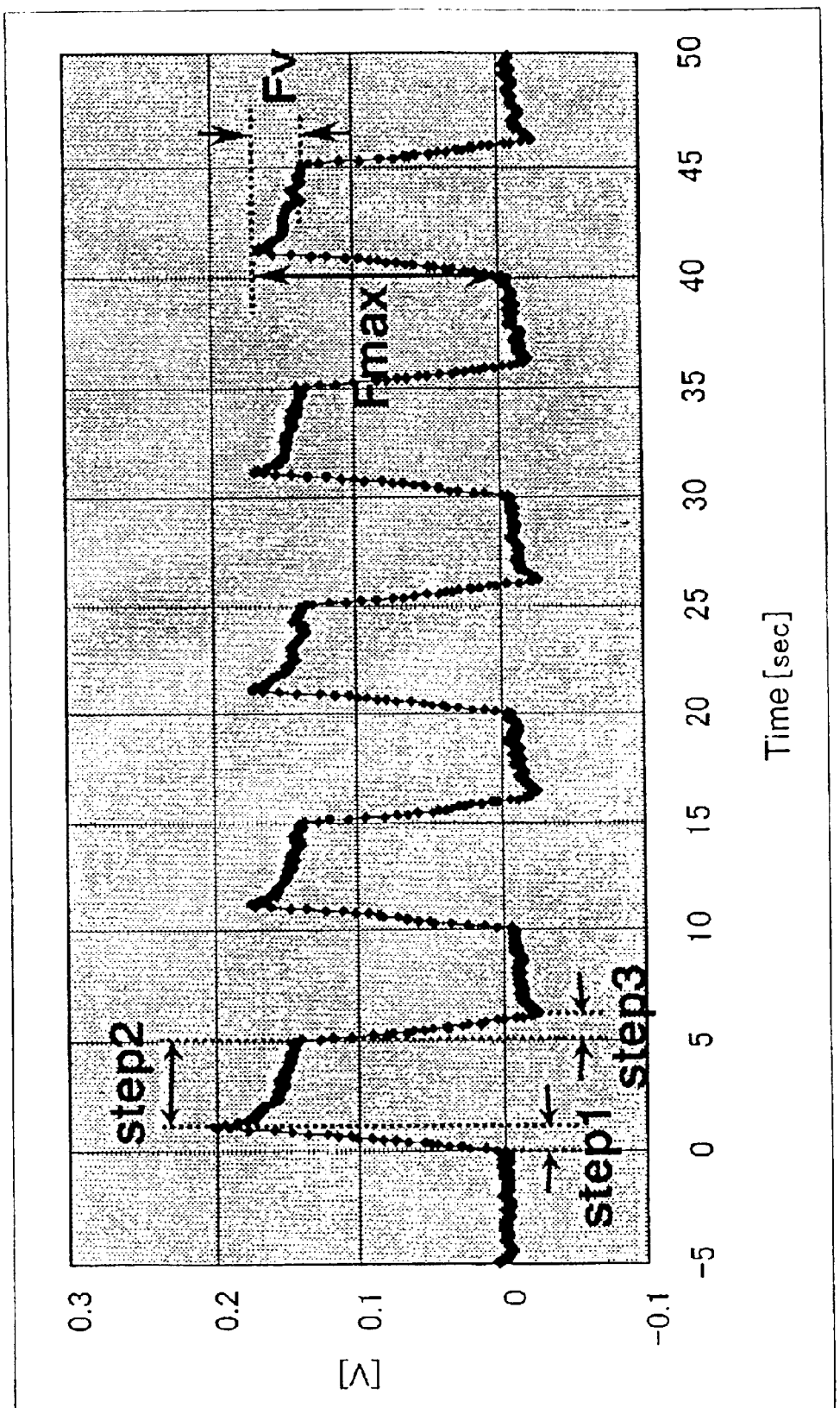
FIG. 7 shows results of measurement of a skin of a human arm in Embodiment 3.

Next, using the above-described device, measurement was performed with seventeen healthy white males and females (in ages of twenty to sixty-one) as subjects in two directions along minor axis and major axis of the arm with respect to two sites, a center of the inner side of the upper arm and a center of the outer side of the forearm. An example of measurement results is shown in FIG. 7. It can be seen that the result shows a pattern of the agarose gel type having viscoelasticity.

Figure 8:
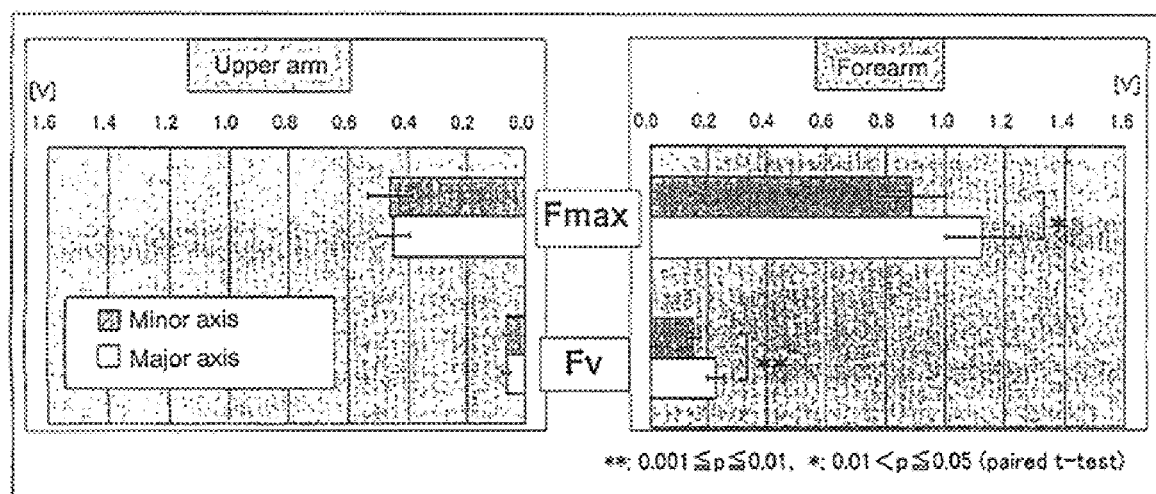
FIG. 8 shows results of calculating average values of parameters Fmax and Fv for each site and direction of measurement.

Results of calculating average values of Fmax and Fv for each site and direction of measurement are shown in FIG. 8. On an inner side of an upper arm, both Fmax and Fv had no significant difference in two directions. However, on an outer side of a forearm, both the parameters had significantly higher values in a long axis direction than in a short axis direction.

In addition, correlation between each parameter and ages is shown in Table. 2. In both the sites, correlation with ages was recognized in Fmax on the inner side of the upper arm and in Fv on the outer side of the forearm, respectively, only in the major axis direction, not in the minor axis.

TABLE 2

| Parameter | Upper arm | | Forearm | |
|---|---|---|---|---|
| | Minor axis direction | Major axis direction | Minor axis direction | Major axis direction |
| Fmax | — | ↓* | — | — |
| Fv | — | — | — | ↑* |

↑: Positive correlation, ↓: Negative correlation
*: $0.01 < p \leq 0.05$, —: $0.05 < p$ (Paired t test)

From the above results, it has been found that, by the measurement using the measurement device of the present invention, the mechanical properties of the skin on the outer side of the forearm that is an exposed site are different in the major axis direction and the minor axis direction, and that changes in mechanical properties of the skin corresponding to aging are recognized in the major axis direction on both the inner side of the upper arm and the outer side of the forearm. That is, a possibility of analyzing connection between changes in mechanical properties corresponding to photoaging and wrinkle formation was indicated by using the measurement device of the present invention.

<Embodiment 4>

The same device as in Embodiment 3 was used except that the motion pattern of the contacts was changed as described below and the guard ring was changed to the one that was formed in a double cylindrical shape, such that an inner cylinder could slide inside an outer cylinder and the inner cylinder was energized by a spring to protrude further than the outer cylinder. Motion pattern of the movable contact Step 1: The distance between the arms is reduced from 4 mm to 3.5 mm (0.5 mm/sec).

Step 2: The distance between the arms is maintained at 3.5 mm for four seconds.

Step 3: The distance between the arms is returned to 4 mm (0.5 mm/sec).

Repeat of the cycle: Five times (the pattern is analyzed for the last cycle)

Figure 9:
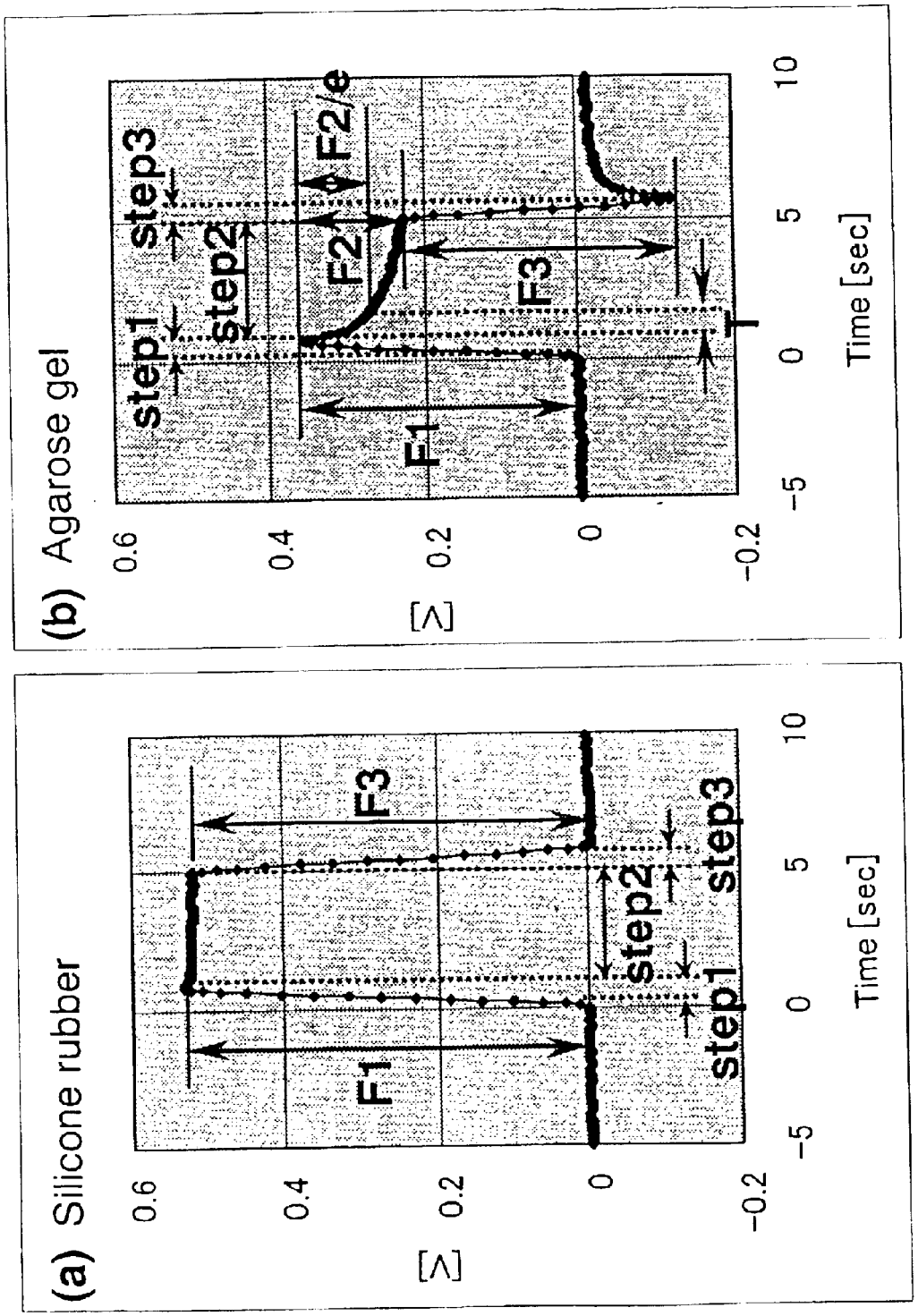
FIG. 9 shows results of measurement of silicone rubber (a) and agarose gel (b) in Embodiment 4.

Silicone rubber was measured as a highly elastic sample and agarose gel was measured as a sample having viscoelasticity using the above-described device. An example of measurement results is shown in FIG. 9. When analyzing was performed using a maximum stress at the time of skin contraction (F1(V) in FIG. 9), a maximum value of a stress attenuating at the time of maintenance of the distance (F2(V) in FIG. 9), a maximum value of a stress decreasing at the time of releasing contraction (F3(V) in FIG. 9) and time until the attenuation of the stress at the time of maintenance reaches F2/e (e=2.718) (T (seconds) in FIG. 9) as parameters, F2 observed in the agarose gel was hardly observed in the silicone rubber. Therefore, F2 and T calculated based on F2 are considered to be parameters relating to viscoelasticity. In addition, it can be seen that F1 and F3 increase dependently on hardness of the silicone rubber or concentration of the agarose gel. Therefore, F1 and F3 are considered to be parameters relating to hardness.

Figure 10:
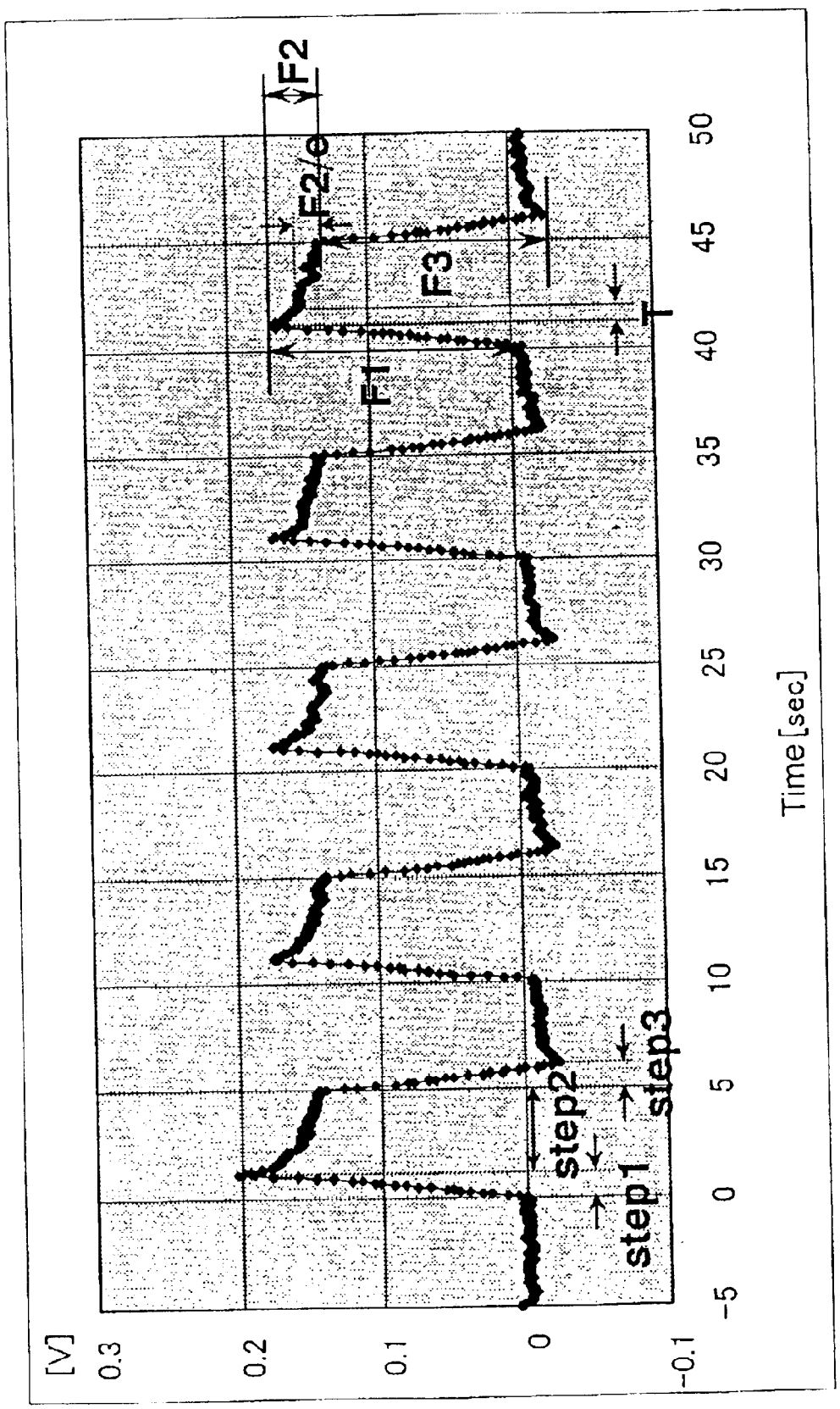
FIG. 10 shows results of measurement of a skin of a human arm in Embodiment 4.

Next, using the above-described device, measurement was performed with eighty healthy Japanese males (in ages of twenty-one to fifty-nine, an average age of 45.3) as subjects targeting outer canthus portions on the face in two directions, horizontal and vertical, with respect to a line connecting an inner canthus and an outer canthus. An example of measurement results is shown in FIG. 10. It can be seen that the result shows a pattern of the agarose gel type having viscoelasticity.

Figure 11:
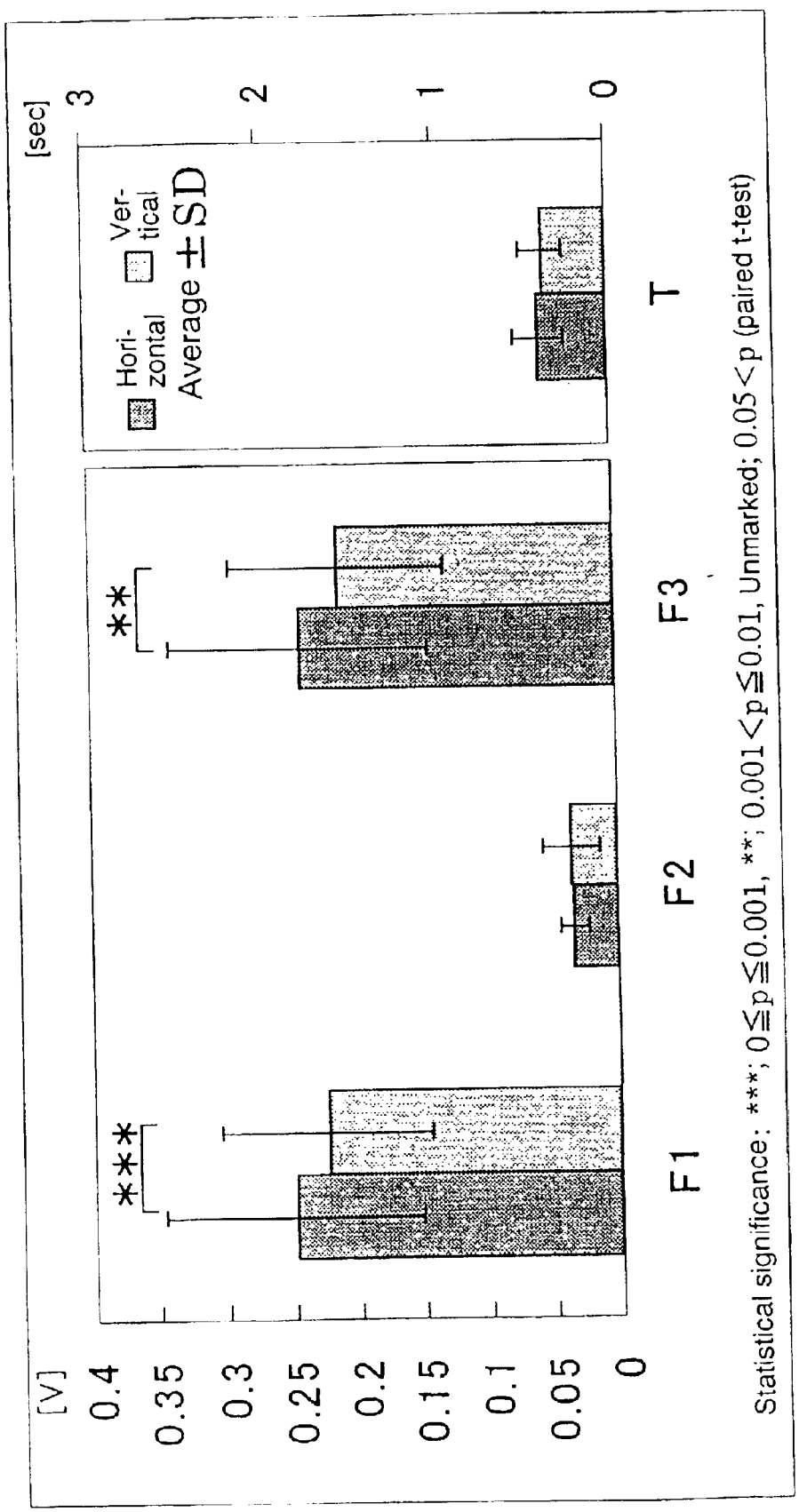
FIG. 11 shows results of calculating average values of parameters F1, F2, F3 and T for each direction of measurement.

A result of calculating average values of F1, F2, F3 and T for each measurement direction is shown in FIG. 11. In the parameters F1 and F3 relating to hardness, values in the vertical direction was significantly lower than those in the horizontal direction. That is, it was found that a significant difference was recognized in mechanical properties relating to hardness in these two directions in the skin of the outer canthus on the face.

In order to examine relationship between the measurement values and degrees of wrinkles of the subjects at this time, light was irradiated diagonally from above at an angle of 20 degrees on a silicone replica of the target site collected at the time of measurement, a percentage of an area of generated wrinkle shadows to an evaluation target area (1 cm×1 cm) is calculated as a wrinkle area ratio by image analysis, and correlation between this ratio serving as an index of evaluation of a degree of a wrinkle and each parameter obtained in the measurement by the measurement device of the present invention was checked.

Results are shown in Table 3. As a result, correlation was recognized only for T in the vertical direction. From this, a possibility of viscoelasticity in the vertical direction relating to wrinkle formation in the outer canthus portion on the face was indicated.

TABLE 3

| Parameter | Correlation with a wrinkle area ratio | |
| --- | --- | --- |
| | Horizontal measurement | Vertical measurement |
| F1 | — | — |
| F2 | — | — |
| F3 | — | — |
| T | — | ** (Negative) |

**: $0 \leq p \leq 0.01$, —: $0.05 < p$ (Test of Alienation of Single Correlation Coefficient)

From the above-described results, it was indicated by the measurement using the measurement device of the present invention that the values of the parameters F1 and F3 relating to hardness are significantly lower in the direction perpendicular to the line connecting the inner canthus and the outer canthus on the skin surface than in the direction parallel to the line in the skin of the outer canthus on the face, and that the mechanical properties of the inner canthus skin are not equal in all the directions.

In addition, as a result of examining the relationship between the measurement values by the measurement device of the present invention and the degrees of a wrinkle in the outer canthus portion on the face, correlation with the degree of a wrinkle in the outer canthus was recognized in the parameter T relating to viscoelasticity in the direction that is perpendicular to the line connecting the inner canthus and the outer canthus on the skin surface, and possibility of this mechanical property affecting wrinkle formation on the outer canthus skin was suggested.

INDUSTRIAL APPLICABILITY

The above-described device for measuring mechanical properties of elastic bodies of the present invention has the following effects.

(1) Since the device has the movable contact, the device can measure mechanical properties of an elastic body while strictly controlling a position and a direction of the contact on the surface of the elastic body. This is particularly preferable for grasping mechanical properties of an elastic body with directionality in mechanical properties such as a skin that has a structure in which fiber bundle structures of collagen being an origin of elasticity line up in one direction under the skin because measurement can be performed for each direction. That is, disturbance or the like of a collagen fiber bundle, which conventionally can only be measured invasively, can be measured non-invasively. In addition to this characteristic, an action pattern of the movable contact is set to include a closing action of the two of the contacts and a stationarily holding action after the closing action, whereby characteristic values suitable for examining connection with wrinkle formation or the like can be measured.

(2) According to the device for measuring mechanical properties of elastic bodies of the present invention, mechanical properties in a form of a combination of mechanical properties attributable to a surface itself of an elastic body and mechanical properties attributable to an inner structure of the elastic body can be measured. Moreover, in a pattern analysis of changes in numerical values of the mechanical properties, the mechanical properties are obtained as multidimensional data that can resolve a variety of factors rather than as a one-dimensional numerical values as in the Cutometer.

What is claimed is:

1. A device for measuring physical properties of skin, comprising:

at least two contacts adapted to contact a skin surface to be measured, at least one of said contacts being a movable contact;

a drive section for moving said movable contact;

a control section for controlling an action of said drive section;

a detecting section for detecting a stress generated by the movement of said contact as an electric signal; and a processing section for processing the electric signal for the stress detected by said detecting section and an amount of movement of said movable contact, wherein the action of said contacts making contact with the surface of said skin includes a closing action of the two of the contacts and a stationarily holding action after the closing action.

2. The device for measuring physical properties of in according to claim 1, which further comprises a display section for displaying data processed by said processing section.

3. The device for measuring physical properties of skin according to claim 2, which comprises a holding section for holding said skin to be measured.

4. The device for measuring physical properties of skin according to claim 1, wherein a probe is comprised of said contacts, said drive section and said detecting section, and the device comprises an arm section for holding a position of said probe.

5. The device for measuring physical properties of skin according to claim 1, which comprises a holding section for holding said skin to be measured.

6. The for measuring physical properties of skin according to claim 1, wherein said contacts are fixed on the surface of said skin.

7. The device for measuring mechanical physical properties of skin according to claim 2, wherein said contacts are fixed on the surface of said skin.

8. The device for measuring physical properties of skin according to claim 2, wherein a probe is comprised of said contacts, said drive section and said detecting section, and the device comprises an arm section for holding a position of said probe.

* * * * *